(12) United States Patent
Sato et al.

(10) Patent No.: US 6,377,896 B1
(45) Date of Patent: Apr. 23, 2002

(54) METHOD AND APPARATUS FOR DETERMINATION OF A SUBSTANCE COEXISTING WITH ANOTHER SUBSTANCE

(75) Inventors: Yoshiharu Sato; Hisashi Okuda, both of Kyoto (JP)

(73) Assignee: Kyoto Daiichi Kagaku Co., Ltd., Kyoto (JP)

( * ) Notice: Subject to any disclaimer, the term of this patent is extended or adjusted under 35 U.S.C. 154(b) by 0 days.

(21) Appl. No.: 09/225,321

(22) Filed: Jan. 5, 1999

(30) Foreign Application Priority Data

Jan. 6, 1998 (JP) .......................................... 10-013450

(51) Int. Cl.⁷ .......................................... G01N 33/487
(52) U.S. Cl. .......................................... 702/23; 436/808
(58) Field of Search ...................... 702/23, 22; 356/39; 436/808; 128/92

(56) References Cited

U.S. PATENT DOCUMENTS

| | | | |
|---|---|---|---|
| 4,436,812 A | | 3/1984 | Endoh et al. .................. 435/14 |
| 4,477,314 A | * | 10/1984 | Richter et al. .................. 204/1 |
| 5,497,772 A | * | 3/1996 | Schulman et al. .......... 128/635 |

FOREIGN PATENT DOCUMENTS

| | | |
|---|---|---|
| DE | 42 21 848 | 5/1994 |
| EP | 0 404 594 | 12/1990 |
| JP | 9-292387 | 11/1997 |

OTHER PUBLICATIONS

English Abstract, Patent Abstracts of Japan, Publication No. 09-292387, Nov. 11, 1997.
M. Obuchi et al., "Comparison of Simple Assay Systems for SMBG Equipped with Biosensor and Oxygen Electrode, and Effect of the Collecting Tube for Blood," *Analysis of Biosample*, vol. 17, No. 13 (1994).

* cited by examiner

*Primary Examiner*—Marc S. Hoff
*Assistant Examiner*—Edward Raymond
(74) *Attorney, Agent, or Firm*—Finnegan, Henderson, Farabow, Garrett & Dunner, L.L.P.

(57) ABSTRACT

A measuring method for determination of the content of a substance in a specimen on the basis of the value of a physical property measured with the specimen in which the determination is influenced by another substance coexisting with the object substance in the specimen, characterized in that: the value of the physical property measured with the specimen with a known content Ht of the coexisting substance is corrected to a value Vc of the physical property calculated with a standard content value Hts as the content Ht of the coexisting substance on the basis of a correction table showing the relationship between the contents Ht of the coexisting substance and set values V of said physical property for the respective key contents of the object substance. The measuring method permits instantaneous determination with high precision of the content of a substance for which no calibration curve can be prepared because of the effects of a coexisting substance.

10 Claims, 1 Drawing Sheet

METHOD AND APPARATUS FOR DETERMINATION OF A SUBSTANCE COEXISTING WITH ANOTHER SUBSTANCE

BACKGROUND OF THE INVENTION

1. Field of The Invention

The present invention relates to a method and apparatus for determination of the content of a substance contained in a specimen containing another coexisting substance which can have effects on the determination. More particularly, the present invention relates to a method and apparatus for handy and quick determination of blood sugar in the medical field.

2. Related Art

It often happens that accurate determination of the content of a substance in a specimen is impossible because of the effects of another substance present in the specimen. An example is a blood sugar determination system in which a dry reagent is reacted with blood or the specimen, in what is called dry chemistry. The dry chemistry is popular for use in determination of blood sugar in blood analysis, as in an emergency and before medical examination, and is sometimes conducted by the patient himself or herself, because it does not need liquid reagents which require special skill in handling, preparation or disposal and can be practiced without expensive equipment.

In the prior art, the reflectance determination technique and the immobilized enzyme electrode technique have been known for use in blood sugar determination systems utilizing dry chemistry.

The reflectance determination technique, which employs a test strip with a coloring reagent fixed in it, is reacted with a specimen, and the strip changes in color. This color change is measured by reflectance of a light ray emitted from a light source.

The immobilized enzyme electrode technique uses a test strip with electrodes formed on it for determination of blood sugar. In this technique glucose oxidase (GOD) and potassium ferricyanide as an electron carrier are fixed or immobilized on the electrodes. GOD oxidizes the glucose in blood into gluconic acid and at the same time imparts electrons to ferricyanide ions which then turn Into ferrocyanide ions. When a voltage is applied between the two electrodes, the ferrocyanide ions give electrons to the positive electrode and turn back into ferricyanide ions, producing electric current. The strength of this electric current is measured For determination of lactic acid, rather than glucose, the test strip has lactic acid oxidase (LOD) immobilized on it, instead of GOD. The electron carrier is not limited to ferricyanide ions. It may be ferrocene.

In either of the above techniques, however, measurements are affected by the amount of solid matters (in the case of blood sugar determination, chiefly red blood corpuscles), because the determination object in the specimen is liquid components (in the case of blood sugar determination, chiefly serum). That is, in the reflectance determination technique, as the solid matters increase, the relative amount of liquid components decreases, slowing down the dissolution velocity and the coloring. In the immobilized enzyme electrode technique, the solid matters stick to the electrodes, reducing the effective area of the electrodes. In both of the prior art techniques, therefore, the calculated content of a substance arrived at on the basis of measurements becomes increasingly lower than the true value as the solid matters increase. A possible solution to this problem may be to have a calibration curve prepared which relates the solid contents to the measurements, and to correct the measurements on the basis of that calibration curve.

However, the correlation between the solid contents and the measurements is different, depending on the true contents of the object substance, and can not be put to a primary regression, a secondary regression or a multivariate analysis. And it is impossible to have the correlation stored in the apparatus. In determination systems based on dry chemistry, the effects of coexisting substances in specimens could not be automatically eliminated in the measuring apparatus.

SUMMARY OF THE INVENTION

It is an object of the present invention to provide a measuring method and apparatus which permit automatic compensation for effects of coexisting substances on the measurement of object substances in specimens.

To attain the foregoing object, the present invention provides a measuring method for determination of the content of an object substance in a specimen on the basis of the value of a physical property measured with the specimen, in which the determination is influenced by another substance coexisting in the specimen with the object substance, characterized in that:

the value of the physical property measured with the specimen in which the content (hereinafter referred to as "Ht") of the coexisting substance is known is corrected to a value (hereinafter referred to as "Vc") of the physical property calculated with a standard content value (hereinafter referred to as "Hts") as the content the of Ht of the coexisting substance on the basis of a correction table showing the relationship between the contents Ht of the coexisting substance and the values (hereinafter referred to as "V") of the aforesaid physical property set for the respective key or base contents of the object substance.

This measuring method uses a specimen in which the content Ht of the coexisting substance is a known content (hereinafter referred to as "Htk"). An example is blood. In case the content Ht of the coexisting substance is not known, it should be determined in some suitable method or apparatus beforehand. If the content of a coexisting substance such as the hematocrit, that is, the volume percentage of erythrocytes in whole blood is peculiar to the sampling source, the determination has to be done only in the initial stage, because that initially determined value can be used afterward.

Using that specimen, the aforesaid physical property is determined. The physical property is not restrictive, but any will do as long as it changes with the content of an object substance in a specimen. The physical properties that can be utilized are not limited to intrinsic properties found in original specimens alone, such as the transmittance of light, but include extrinsic properties, such as the reflectance of light, in a specimen after it is reacted with a coloring reagent and the electric current and voltage that can be produced and measured after the specimen is reacted with a redox reagent. For purpose of simplification, it is to be understood that the measured value of the physical property is represented by "Vm". Also, it is assumed that the aforesaid correction table is prepared and ready for use. As to the relationship between the contents Ht of the coexisting substance and the set values V of the physical property in the correction table, it can be established this way: The aforesaid physical property is determined for a variety of specimens with the known contents of both the object substance and the coexisting substance. The values of the physical property thus obtained are enumerated as set values of the physical property in the table. For purpose of simplification, it is to be understood that the contents Ht of the coexisting substance and the set values V of the physical property are related to each other with the set values of the physical property enumerated in the row for each content G of the object substance and in the column for each content Ht of the coexisting substance in the correction table. In this correction table, the known quantities G of the object substance are a parameter. The direction of arrangement is not restrictive.

In the next step, the measured value Vm is corrected to a value of the physical property calculated with the standard value Hts as the content Ht of the coexisting substance. Such correction is usually done as follows. The first procedure is to work out two values V of the physical property nearest to the measured value Vm of the physical property under a known content value Hts of the coexisting substance by proportional distribution of data in the correction table, one of the two values found in the upper row and the other in the lower row. From those two values V, the value V under the standard value Hts of the content of the coexisting substance is found in the row of the measured value Vm. Then, the content of the object substance can be derived from the found value V under the standard content Hts using the calibration curve. But in case the calibration curve is poor in linearity, a main table is prepared beforehand which shows the relationship between the values V of the physical property and the corresponding contents of the object substance. On the basis of that main table, the content of the object substance may be derived. As set forth above, the measured value Vm is first corrected to the value under the standard content Hts on the basis of the correction table, and then the content of the object substance is derived from the corrected value Vc. Thus, the content of the object substance can be worked out with high precision irrespective of the effects of the content Ht of the coexisting substance.

A measuring apparatus suitable for practicing the measuring method of the present invention is an apparatus to determine the content of an object substance in a specimen on the basis of the value of a physical property measured using the specimen in which the measurements are affected by the content of a substance coexisting with the object substance in the specimen, said apparatus comprising:

a correction table showing the relationship between the contents Ht of the coexisting substance and the set values V of the aforesaid physical property for the respective key or base contents of the object substance, a Htk file to store specific known content values Htk of the coexisting substance; and an arithmetic means to correct the value of the aforesaid physical property measured using the specimen to a value calculated with a specific standard value Hts as the content Ht of the coexisting substance on the basis of the correction table and the known content value Htk of the coexisting substance.

The correction table is generally stored in a storage unit. Once it is prepared, a correction table will have to be used until it is revised, and therefore it should be stored in a read-only memory (ROM). The known content value Htk of the coexisting substance is different for different specimens and has to be renewed each time a determination is made. Therefore, it should be stored in a random access memory (RAM). In case sampling is repeated at the same source, however, the known content value Htk does not have to be renewed each time, because there is no difference between specimens as long as the sampling source is the same. In case the content of the object substance is to be derived from the aforesaid corrected value Vc on the basis of the main table, the main table should be stored in the same storage unit where the correction table is stored. The arithmetic means is usually formed of a CPU and a computer program. An equivalent control circuit may serve the purpose, too.

The measuring method according to the present invention permits instantaneous determination with high precision of the content of a substance for which no calibration curve can be prepared because of the effects of a coexisting substance.

DESCRIPTION OF THE PREFERRED EMBODIMENTS

Figure 1:
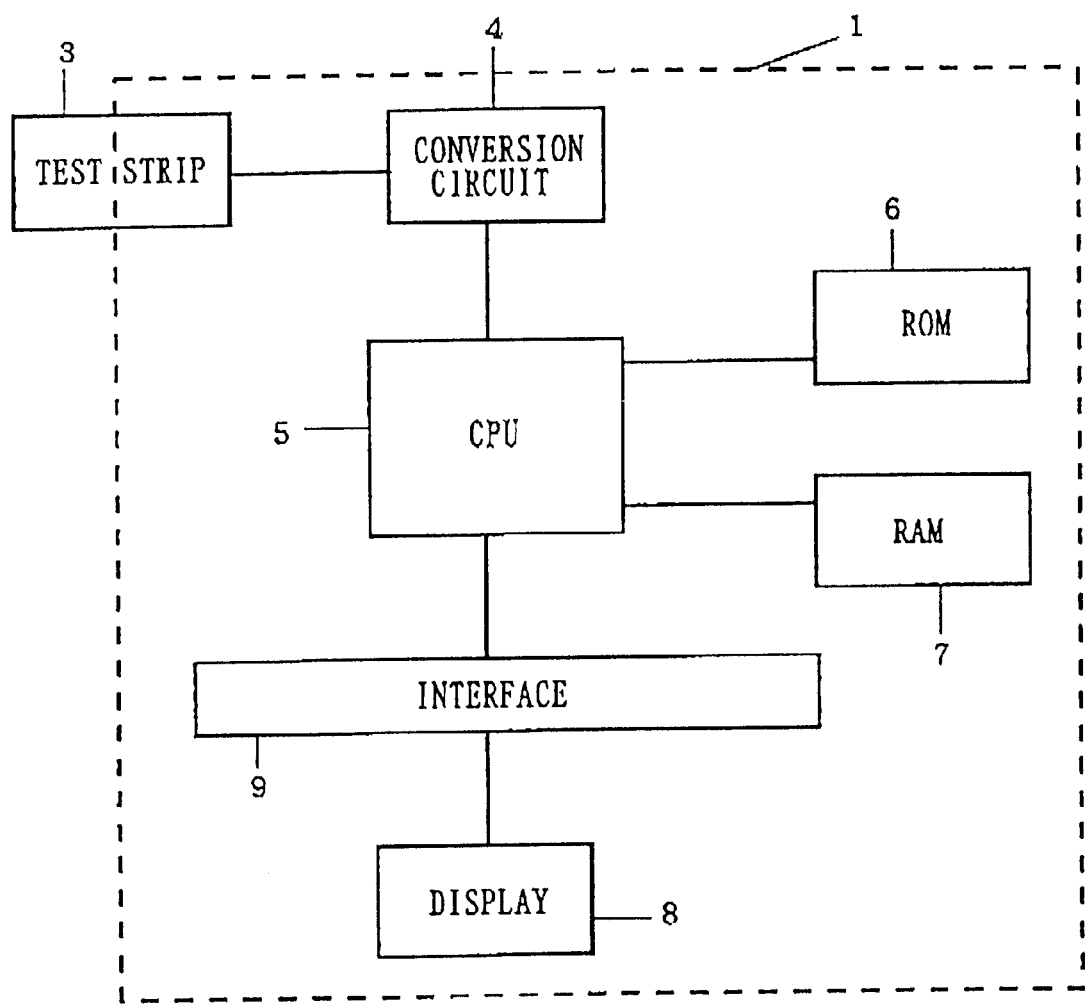
FIG. 1 is a block diagram schematically showing the configuration of a measuring apparatus embodying the present invention.

The aforesaid object substance is, say, glucose, and the coexisting substance is, say, a blood cell element if the coexisting substance is red blood corpuscle, the content thereof is especially expressed in hematocrit. The hematocrit is peculiar to each person. As long as a measuring apparatus is to be used exclusively for a specific person, the known value Htk, once it is stored in a file, does not have to be renewed each time. The aforementioned physical property is preferably an electric current arising from an oxidizing reaction of glucose. Since the blood sugar level is related to the strength of an electric current produced, a high precision determination of blood sugar is possible.

FIG. 1 shows the configuration of a blood sugar measuring apparatus embodying the present invention. This apparatus works on the immobilized enzyme electrode technique principle. The apparatus 1 comprises a main unit 2 and a test strip 3. The test strip 3 has electrodes formed on it. Glucose oxidase (GOD) and an electron carrier potassium ferricyanide are fixed on the electrodes. The main unit 2 is provided with a conversion circuit 4 to convert the electric current outputted from the test strip into voltage and then a digital value, a central processing unit (CPU) 5, a read-only memory (ROM) 6, a random access memory (RAM) 7 and a display 8. The test strip 3 is provided with a pair of electrodes on which GOD and potassium ferricyanide are fixed. RAM 7 has an Htk file stored in it. ROM 6 stores a correction table, a main table and a specific program. The program derives the content of the object substance on the basis of those tables, the output of the conversion circuit 4 and the known value Htk of the coexisting substance, and shows the results or the content of the object substance on the display 8 through an interface 9.

EXAMPLE 1

This example describes the determination of the blood sugar level in a patient with a hematocrit of 39 percent. Table 1 is stored in ROM as correction table. The table enumerates voltages as set values Vs converted from electric current levels—electric current levels arising in the oxidizing reaction—which were measured with a number of blood specimens with different known hematocrits and known key blood sugar levels. The respective set values V of the physical property for G50 or a glucose concentration of 50 percent are values obtained by amplifying the respective measurements at specific amplification rates with the voltage for that glucose concentration at a hematocrit of 45 percent adjusted to 40 mV. The voltages for higher glucose concentrations—G100 to G600—are amplified likewise.

TABLE 1

| Ht | 20 | 25 | 35 | 45 (standard) | 55 | 65 |
|---|---|---|---|---|---|---|
| G50 | 41.4 | 41.1 | 40.6 | 40.0 | 39.4 | 38.9 |
| G100 | 72.5 | 72.0 | 71.0 | 70.0 | 69.0 | 68.0 |
| G200 | 135.3 | 132.2 | 126.1 | 120.0 | 113.9 | 107.8 |
| G400 | 236.7 | 231.4 | 220.7 | 210.0 | 199.3 | 188.6 |
| G600 | 349.5 | 341.6 | 325.8 | 310.0 | 278.2 | 278.4 |

The output Vm of the conversion circuit 4 before correction is 45 mv, for example. In Table 1, the patient's hematocrit Htk=39 is located between Ht=35 and Ht=45, while the measured value Vm=45 is between the row of V 40.0 and the row of V=70.0 as shown in Table 2. The problem is now to find z in Table 2.

TABLE 2

| Ht | 35 | 39 | 45 (standard) |
|---|---|---|---|
| G50 | 40.6 | x | 40.0 |
|  |  | 45 | z |
| G100 | 71.0 | y | 70.0 |

First, x is to be found. Solving the equation (40.0−40.6)/(45−35)=(40.0−x)/(45−39), it is found that x=40.36. Similarly, it is found that y=70.60. The obtained values of x and y are substituted in the equation (70.0−40.0)/(y−x)=(z −40.0)/(45−x), and it is found, that z=44.6. This result is then checked against the data in the main table, and the content of the object substance or the blood sugar level is found by proportional distribution. The main table is Table 3, and is stored in ROM. A number of main tables, one for each new production lot of the test strip, are prepared beforehand so that the one fittest for the test strip used may be selected. That calculation is carried out instantaneously by the CPU.

TABLE 3

| V | Glu |
|---|---|
| 40.0 | 50 |
| 70.0 | 100 |
| 120.0 | 200 |
| 210.0 | 400 |
| 310.0 | 600 |

EXAMPLE 2

This example describes the determination of the blood sugar level in a patient with a hematocrit of 28 percent. The output Vm of the conversion circuit 4 before correction is 45 mv, for example. The procedure in this example is the same as in Example 1 except that x, y and z in Table 4 are calculated in Example 2 instead. Solving the equation (40.6−41.1)/(35−25)=(40.6−x)/(35 −28), it is found that x=40.95. Similarly, it is found that y=71.70. The obtained values of x and y are substituted in the equation (70.0−40.0)/(y−x) (z−40.0)/(45−x), and it is found that z=43.95.

What is claimed is:

1. A measuring method for the determination of the content of an object substance in a specimen, on the basis of the value of a physical property measured with the specimen, in which the determination is influenced by another substance coexisting in the specimen with the object substance, the measuring method comprising:

measuring the value of the physical property with the specimen in which the content (Ht) of the coexisting substance is known;

preparing a correction table showing the relationship between the content (Ht) of the coexisting substance and the values (V) of the aforesaid physical property set for the respective key contents of the object substance; and correcting the measured value of the physical property to a corrected value (Vc) of the physical property calculated with a standard content value (Hts) as the content (Ht) of the coexisting substance on the basis of the correction table and the known contents (Htk) of the coexisting substance.

2. The measuring method of claim 1, further comprising deriving the content of the object substance from said corrected value (V) and a main table showing the relationship between the set values (Vs) with the standard content value (Hts) as the content (Ht) of the coexisting substance and the contents of the object substance corresponding to said set values (V).

3. The measuring method of claim 1, wherein the object substance is glucose and the coexisting substance is a blood cell component.

4. A measuring method of claim 3, wherein said physical property is an electric current arising in an oxidizing reaction of glucose.

5. An apparatus for determining the content of an object substance in a specimen on the basis of the value of a physical property measured with the specimen, in which the measurements are affected by the content of another substance coexisting with the object substance in the specimen, said apparatus comprising:

a correction table showing the relationship between the contents (Ht) of the coexisting substance and the values (V) of the aforesaid physical property set for the respective key contents of the object substance, a file for storing specific known contents (Htk) of the coexisting substance, and an arithmetic means for receiving information from the correction table and the file and correcting the value of a physical property measured with a specimen to a corrected value (Vc) calculated with a specific standard content value (Hts) as the content (Ht) of the coexisting substance on the basis of the correction table and the known contents (Htk).

6. The apparatus of claim 5, further comprising a main table showing the relationship between the set values (V) with the standard value (Hts) as the content (Ht) and the contents of the object substance corresponding to said set values (V), wherein said arithmetic means derives the content of the object substance from said corrected value (Vc) on the basis of said main table.

7. The apparatus of claim 5, wherein the object substance is glucose and the coexisting substance is a blood cell component.

8. An apparatus claim 7, wherein said physical property is an electric current arising in an oxidizing reaction of glucose.

9. The measuring method of claim 1, wherein the set values (V) vary with known contents (G) of the object substance as a parameter.

10. The apparatus of claim 5, wherein the set values (V) vary with known contents (G) of the object substance as a parameter.

* * * * *